(12) United States Patent
Delconte et al.

(10) Patent No.: US 10,377,118 B2
(45) Date of Patent: Aug. 13, 2019

(54) PREPARING LAMINATE MATERIALS FOR TESTING (71) Applicant: The Boeing Company, Chicago, IL (US)

(72) Inventors: John W. Delconte, Westchester, PA (US); Thomas Joseph Gonze, North Charleston, SC (US); Ryan J. Hertel, Media, PA (US); Gina M. Miller, Philadelphia, PA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 15/369,654

(22) Filed: Dec. 5, 2016

(65) Prior Publication Data

US 2018/0154623 A1 Jun. 7, 2018

(51) Int. Cl.
*B32B 43/00* (2006.01)
*B32B 37/12* (2006.01)
*B32B 38/10* (2006.01)
*G01N 19/04* (2006.01)

(52) U.S. Cl.
CPC .............. *B32B 37/12* (2013.01); *B32B 38/10* (2013.01); *B32B 43/006* (2013.01); *B32B 2305/07* (2013.01); *B32B 2313/04* (2013.01); *G01N 19/04* (2013.01); *G01N 2203/0298* (2013.01); *Y10T 156/1168* (2015.01); *Y10T 156/1184* (2015.01); *Y10T 156/1961* (2015.01); *Y10T 156/1967* (2015.01)

(58) Field of Classification Search
CPC . B32B 38/10; B32B 43/006; Y10T 156/1168; Y10T 156/1184; Y10T 156/1961; Y10T 156/1967

USPC ................................ 156/714, 717, 761, 762
See application file for complete search history.

(56) References Cited

U.S. PATENT DOCUMENTS 2,444,097 A * 6/1948 Grant ...................... B25B 27/16
254/100
3,866,883 A * 2/1975 Goransson .............. B28B 13/04
254/93 R (Continued)

OTHER PUBLICATIONS

Varun Ratta, Crystallization, Morphology, Thermal Stability and Adhesive Properties of Novel High Performance Semicrystalline Polymides Thesis, Chapter 7—Wedge and Double Cantillever Beam Tests on a High Temperature Melt Processable Polymide Adhesive, TPER-BPDA-PA, Apr. 26, 1999, pp. 221-242.

(Continued)

*Primary Examiner* — Mark A Osele
*Assistant Examiner* — Nickolas R Harm
(74) *Attorney, Agent, or Firm* — Kolisch Hartwell, P.C.

(57) ABSTRACT

Methods of preparing laminate test samples for subsequent testing, including positioning the test sample within a fixture body, securing the test sample within the fixture body, applying a separating force to urge a first layer portion of the test sample away from a second layer portion of the test sample, and separating the first layer portion from the second layer portion to create a predetermined separation length along the test sample, provided that the predetermined separation length is established by an interaction between the fixture body and the test sample as the first layer portion is separating from the second layer portion.

21 Claims, 6 Drawing Sheets

(56) References Cited

U.S. PATENT DOCUMENTS

| | | | | |
|---|---|---|---|---|
| 4,924,708 A * | 5/1990 | Solomon | G01N 3/08 | 73/799 |
| 4,926,694 A * | 5/1990 | Crews, Jr. | G01N 3/20 | 73/794 |
| 5,367,762 A * | 11/1994 | Disko | H01L 21/67126 | 29/426.4 |
| 5,386,442 A * | 1/1995 | Diaz | G01N 3/10 | 376/245 |
| 6,068,727 A * | 5/2000 | Weaver | H01L 21/67092 | 156/701 |
| 6,074,163 A * | 6/2000 | Yamazaki | B65G 49/06 | 271/97 |
| 7,150,804 B2 * | 12/2006 | Tajima | G09F 7/18 | 156/707 |
| 7,187,162 B2 * | 3/2007 | Kerdiles | G01N 19/04 | 156/765 |
| 2008/0274326 A1 * | 11/2008 | Kim | B29C 70/24 | 428/90 |
| 2009/0107629 A1 * | 4/2009 | Oguri | B24C 1/06 | 156/279 |
| 2009/0166930 A1 * | 7/2009 | Fujita | B32B 38/10 | 264/334 |
| 2009/0241682 A1 * | 10/2009 | Costa Balanzat | G01N 3/04 | 73/860 |
| 2013/0189888 A1 * | 7/2013 | Patrick | B29C 73/22 | 442/71 |
| 2014/0196855 A1 * | 7/2014 | Iizuka | B32B 43/006 | 156/761 |
| 2014/0326074 A1 * | 11/2014 | Van Voast | G01N 19/04 | 73/827 |
| 2015/0202857 A1 * | 7/2015 | Morikazu | B32B 43/006 | 156/751 |

OTHER PUBLICATIONS

Ian Hamerton, Double cantilever beam testing of repaired carbon fibre composites, Article in Composites Part A Applied Science and Manufacturing, Jun. 2000, 7 pages.

David J. Macon, Nonlinear Elastic J-Integral Measurements in Mode I Using a Tapered Double Cantilever Beam Geometry, Article acquired from NASA Marshall Space Flight Center, Jan. 2006, 33 pages.

ASTM International, Designation: D5528-13, Standard Test Method for Mode I Interlaminar Fracture Toughness of Unidirectional Fiber-Reinforced Polymer Matrix Composites, Published Nov. 2013, 13 pages.

* cited by examiner

PREPARING LAMINATE MATERIALS FOR TESTING

FIELD

This disclosure relates to testing of laminate materials for interlaminar adhesion. More specifically, the disclosure relates to methods of introducing a precrack in laminate test materials prior to interlaminar adhesion testing.

INTRODUCTION

Laminate materials are prepared by adhering two or more layers together into a single material. The layer materials used to prepare laminate materials may be the same or different, depending on the processes and the object to be laminated. Familiar examples of laminate materials include the safety glass typically used in automobiles, in which a plastic film is sandwiched between two sheets of glass, and engineered wood products such as Laminated Veneer Lumber (LVL), which is assembled from multiple thin sheets of wood veneer.

Of particular importance in modern manufacturing are composite laminate materials, which typically include two or more layers prepared from composite materials. Composite materials may include a matrix (or bonding) material, such as a thermoset resin, and a reinforcement material, for example such as a plurality of fibers (e.g., glass or carbon fibers). The composite layers may be joined using an adhesive to form a composite laminate material. Composite laminate materials may be employed in applications where certain structural properties are required, such as in-plane stiffness, bending stiffness, strength, and coefficient of thermal expansion, among others.

As it may be critical that a selected composite laminate material possess the desired structural properties, samples of composite laminate materials may be routinely subjected to testing during product development or as quality assurance during product manufacture. Although a given laminate sample may be interrogated via a number of such tests, the measurement of interlaminar fracture toughness may be of particular importance. The measurement of a selected laminate's susceptibility to interlaminar fracture, or delamination, may be employed to determine the damage tolerance of a laminate sample, and in general to provide quantitative feedback on the effects of a change in the raw materials employed, or in a manufacturing technique, or to develop criteria for assessing a delamination failure.

Figure 1:
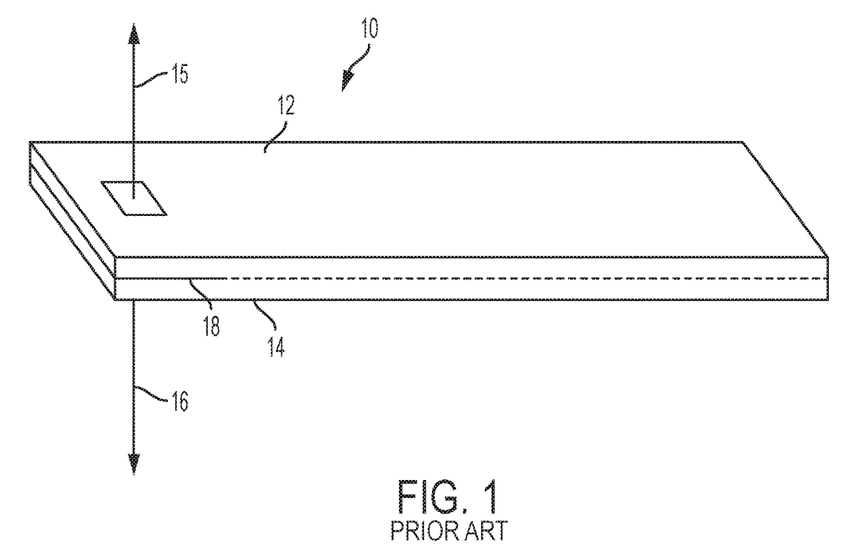
FIG. 1 depicts a laminate material undergoing a Double Cantilevered Beam test useful for measuring interlaminar fracture resistance.

One means of testing for interlaminar fracture resistance is a Double Cantilever Beam (DCB) test, as depicted in FIG. 1 and as described in ASTM D5528. The DCB test quantifies a laminate material's resistance to delamination, or crack propagation, while tensile force is applied normal to the plane of the layers of the material. Referring to FIG. 1, the Double Cantilever Beam test treats a rectangular, beam-shaped laminate material sample 10 as two cantilevered beams 12 and 14 that are separated by applying a load (15, 16) to each beam, gradually increasing the length of crack 18 between beams 12 and 14. The interlaminar fracture toughness can be determined from measurements of load, displacement, and length measurements of crack 18.

Unfortunately, the force required to initiate the crack 18 between beams 12 and 14 can have little relevance to the forces required to achieve a more controlled crack propagation, such as occurs during the DCB test. For this reason an initial separation, or "pre-crack", is typically created between the two layers of interest in a controlled fashion.

What is needed is a method for reproducibly creating a standardized pre-crack for laminate samples prior to interlaminar fracture testing.

SUMMARY

The present disclosure provides methods of preparing laminate materials for subsequent testing.

In some embodiments, the disclosure may provide a method a method of preparing a laminate material test sample, including positioning the test sample within a fixture body, securing the test sample within the fixture body; applying a separating force to urge a first layer portion of the test sample away from a second layer portion of the test sample; and separating the first layer portion from the second layer portion to create a predetermined separation length along the test sample, provided that the predetermined separation length is established by an interaction between the fixture body and the test sample as the first layer portion is separating from the second layer portion.

In some embodiments, the disclosure may provide a method of preparing an elongate laminate sample for interlayer adherence testing, where the laminate sample has at least a first horizontal layer and a second horizontal layer that are at least partially attached to one another, the method including inserting the elongate laminate sample into a clamping fixture that is configured to substantially enclose the laminate sample on four sides orthogonal to the longitudinal axis of the laminate sample, positioning the laminate sample within the clamping fixture so that a placement of a substantially straight edge of the clamping fixture corresponds to a predetermined interlayer separation length and the substantially straight edge of the clamping fixture is oriented at normal to the longitudinal axis of the laminate sample, compressing the laminate sample with the clamping fixture across the width of the laminate sample, and applying a separating force on the first horizontal layer and the second horizontal layer of the laminate sample that is sufficient to separate the layers to a predetermined separation length.

In some embodiments, the disclosure may provide a method of precracking a composite laminate preparatory to double cantilever beam adherence testing of the composite laminate, and the method may include inserting the composite laminate into a clamping fixture that secures the test sample by substantially enclosing the test sample on four sides, clamping the composite laminate by urging an inner face of the clamping fixture against a surface of the composite laminate where the inner face has a straight edge that extends across the width of the composite laminate, and applying a separating force on the composite laminate sufficient to form a predetermined precrack in the composite laminate.

Features, functions, and advantages recited herein may be achieved independently in various embodiments of the present disclosure, or may be combined in yet other embodiments, further details of which can be seen with reference to the following description and drawings.

DESCRIPTION

The present disclosure is directed to methods for preparing laminate materials for interlaminar adherence testing.

Various embodiments of these methods are described below and illustrated in the associated drawings. Unless otherwise specified, a given method may, but is not required to, include at least one of the structures, components, functionalities, and/or variations described, illustrated, and/or incorporated herein. The following description of various embodiments is merely exemplary in nature and is in no way intended to limit the disclosure, its application, or uses. Similarly, although the embodiments of the clamping fixture body of the disclosure are disclosed as useful for the present methods, unless otherwise specified, a clamping fixture body may include but is not required to include at least one of the structures, components, functionalities, and/or variations described, illustrated, and/or incorporated herein. The advantages provided by the embodiments, as described below, are illustrative in nature and not all embodiments may provide the same advantages or the same degree of advantages.

The laminate materials disclosed herein include at least two layers bonded together into a single material, and it is the adherence between the at least two layers that is tested by interlaminar adherence testing. A laminate material may include more than two layers, and interlaminar adherence testing may be carried out to investigate and/or characterize the nature or quality of the bond between any two adjacent layers in the laminate material of interest. The two adjacent layers of interest in the laminate material may include the same or different material or combination of materials.

One or more layers of the laminate materials of the present disclosure may include a composite material. Composite materials may be prepared from two or more constituent materials with significantly different physical or chemical properties. Typically, the constituent materials include a reinforcement material disposed within a matrix (or bond) material.

Appropriate matrix materials may include polymeric resins, metals or metal alloys, or ceramics, among others. In some aspects of the disclosure, the matrix materials may include epoxies, polyimides, aluminum, titanium, and/or alumina.

The reinforcement material which is supported by the matrix material may take the form of a plurality of fibers, which may be short fibers, or substantially continuous fibers. Typically, where a layer is formed using a composite material, the reinforcement material may be substantially continuous fibers that may be woven, braided, stitched, or otherwise formed into an appropriate reinforcement for the desired layer. The reinforcement material may include any appropriate fiber, such as for example glass fibers, carbon fibers, cellulose fibers, polymer fibers, and silicon carbide fibers, among others. In a particularly preferred aspect of the disclosure, the composite material includes carbon fiber-reinforced polymeric resin.

The presently disclosed methods may be suitable for preparing laminate materials for analysis of interlaminar adherence, also referred to as interlaminar fracture toughness. The presently disclosed methods may be useful in conjunction with any displacement-based analysis of interlaminar bond strength, including a Double Cantilever Beam (DCB) test as described in ASTM D5528-13 "Standard Test Method for Mode I Interlaminar Fracture Toughness of Unidirectional Fiber-Reinforced Polymer Matrix Composites." As used herein, reference to a DCB test is intended to include those variations of the DCB test that remain useful for testing interlaminar adherence, such as a Tapered Double Cantilever Beam test, among others.

The laminate material to be examined using an interlaminar adherence analysis, as described above, may be modified to have an initial interlaminar separation. This initial separation typically occurs at a terminal end of the laminate material test sample, and may be created by any suitable means, such as urging a wedge between the two layers of interest, or more typically, by incorporating a thin non-bonding film (or shim) between the two layers at the terminal end of the laminate material test sample that prevents the two layers to fully adhere at the terminal end. In one aspect of the present disclosure, the thin non-bonding layer release film includes a perfluorinated polymer, such as a fluorinated ethylene propylene film or a polytetrafluoroethylene film, among others, and the thin film may be positioned during manufacture of the laminate material.

SPECIFIC EXAMPLES, MAJOR COMPONENTS, AND ALTERNATIVES

The following examples describe illustrative methods for preparing a laminate material test sample for a subsequent interlaminar adherence testing. These examples may include descriptions of selected apparatus useful for carrying out the disclosed methods, as well as selected illustrative methods of preparing a laminate material test sample. These specific examples are intended for illustration and should not be interpreted as limiting the entire scope of the present disclosure. Each example may include one or more distinct disclosures, and/or contextual or related information, function, and/or structure.

Example 1

The presently disclosed methods may be carried out in conjunction with a clamping fixture body, also simply referred to as a clamping fixture, that permits a desired pre-crack to be formed in selected laminate material test samples quickly, accurately, and reproducibly. In order to obtain the desired pre-crack in the selected laminate material, the laminate material may first be positioned within the clamping fixture body.

Figure 2:
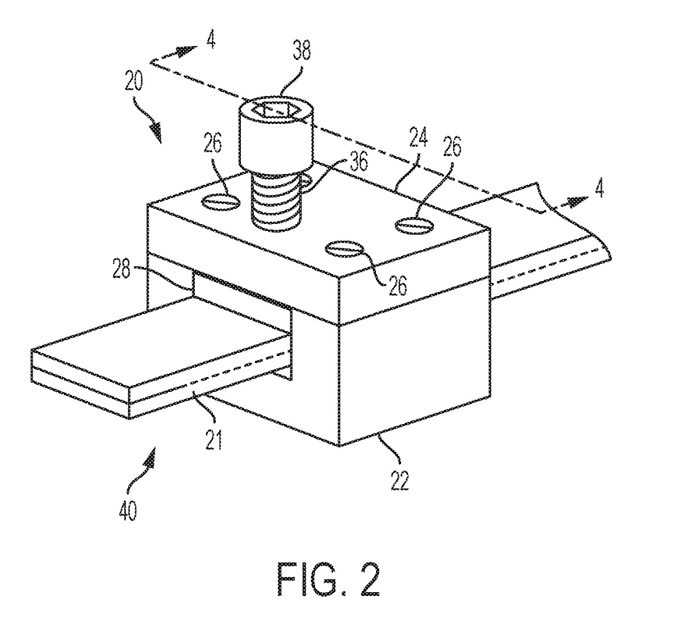
FIG. 2 depicts a laminate material positioned within an illustrative clamping fixture according to the present disclosure.

An illustrative embodiment of a clamping fixture body 20 is shown in FIG. 2 in conjunction with a laminate material 21. The construction and geometry of the clamping fixture body is selected to be complementary to the geometry of the laminate material sample 21 to be tested, which is elongate having four surfaces including a length and a width, where the length is greater than the width, and has a rectangular cross-section. The illustrative clamping fixture 20 is constructed to be complementary to and compatible with laminate material test sample 21, but it should be appreciated that alternative configurations of the clamping fixture body 20 may be utilized that are compatible with alternative test sample geometries.

Figure 3:
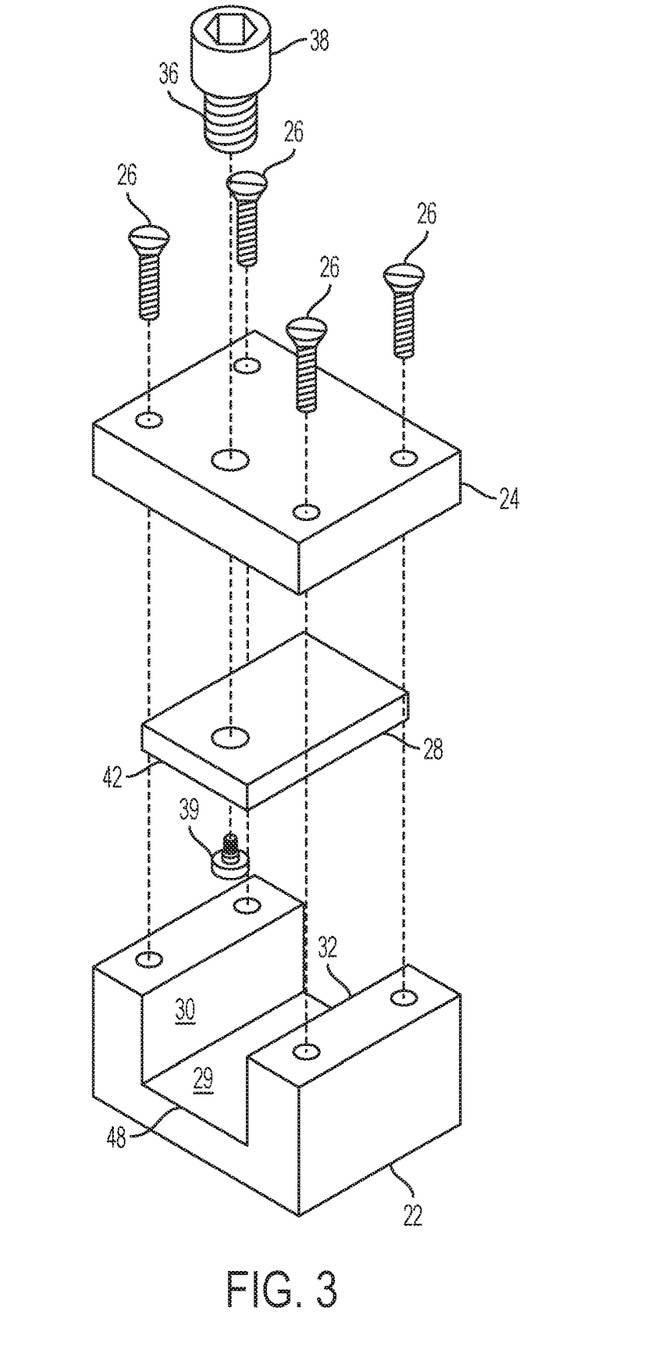
FIG. 3 is an exploded view of the clamping fixture of FIG. 2.

As shown in exploded view in FIG. 3, illustrative clamping fixture body 20 includes a U-shaped base portion 22, a cap portion 24 securely attached to base portion 22 by fasteners 26 and a movable clamping portion 28. U-shaped base portion 22 may define a horizontal surface 29, and two vertical side surfaces 30 and 32. The movable clamping portion 28 may be disposed beneath the cap portion 24 and between side surfaces 30 and 32, and include a flat face 33 parallel with and facing surface 29. By virtue of this construction, surface 29, side surfaces 30 and 32, and face 33 of movable clamping portion 28, in combination, define an internal passage 34 that is configured to receive a selected laminate material test sample 21, and to enclose the laminate material test sample 21 on each of the four sides orthogonal to the longitudinal axis of the laminate material test sample 21, thereby securing the test sample.

Movable clamping portion 28 may be movably coupled to cap portion 24 via a threaded connector 36 having a head 38. The movable clamping portion 28 may be secured to the threaded connector 36 by a shoulder screw 39, as shown in FIG. 3, which may permit free rotation of the connector 36 while still securing the movable clamping portion 28 to the connector 36. The threaded connector 36 may be coupled with cap portion 24, so that rotation of the threaded connector 36 via head 38 may result in the translation of the movable clamping portion 28 closer to surface 29 of base portion 22, or further away from surface 29 of base portion 22. In this way, rotation of the connector head 38 may result in a clamping of the laminate material 21 between the movable clamping portion 28 and surface 29.

Figure 4:
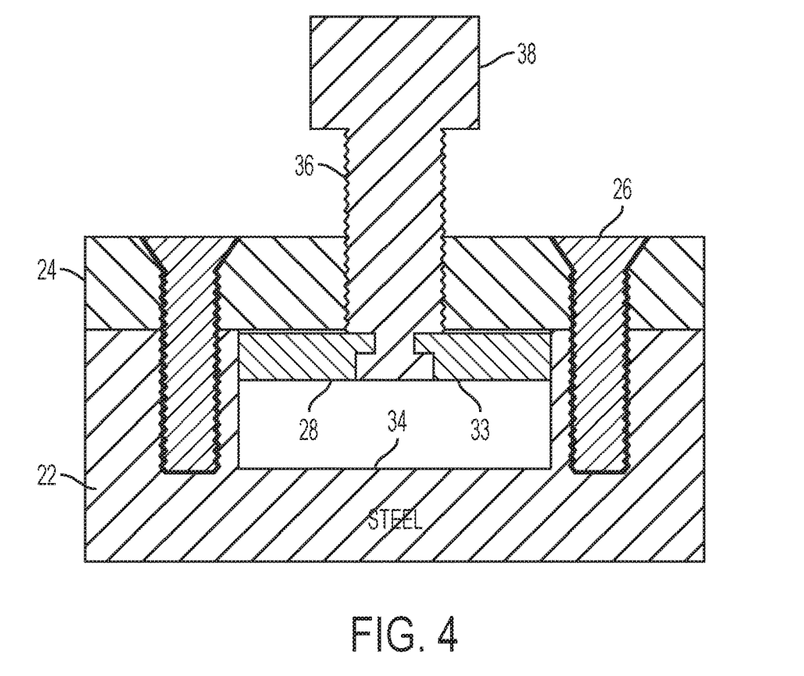
FIG. 4 is a cross-sectional view of the clamping fixture of FIG. 2.
Figure 5:
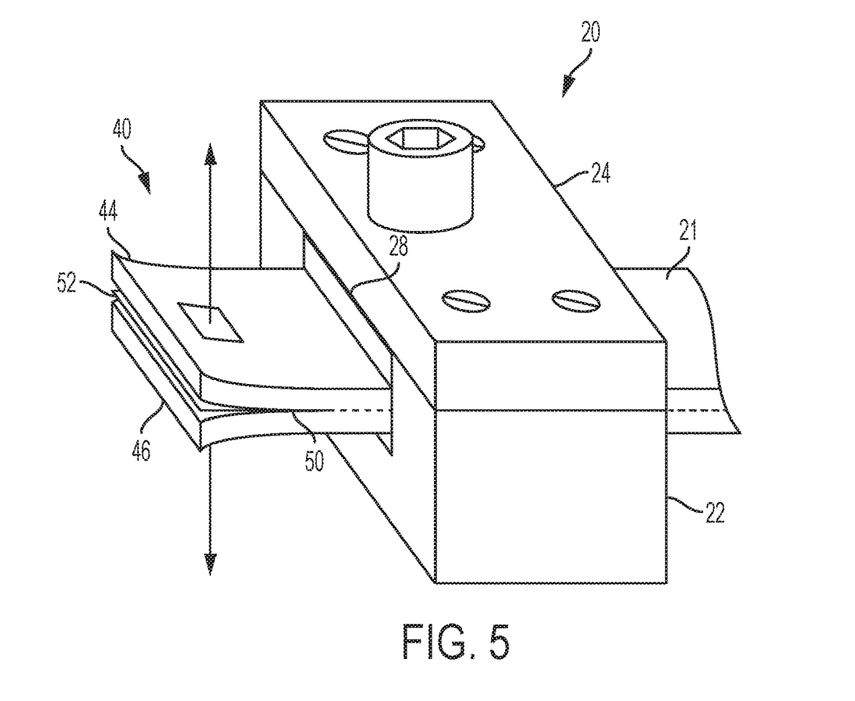
FIG. 5 depicts a laminate material undergoing formation of an interlaminar pre-crack in conjunction with the clamping fixture of FIG. 2.

As shown in FIGS. 4 and 5, by adjusting the position of movable clamping portion 28 relative to base portion 22 by the rotation of connector head 38, the internal passage 34 that is formed thereby may be selected to have a size and shape complementary to the cross-section of the selected elongate laminate material 21, so that the elongate laminate material sample 21 may be inserted into and through the clamping fixture body 20, and a distal terminal portion 40 of the laminate material 21 may projects beyond the clamping fixture 20. The laminate material sample 21 may be inserted by passing the distal terminal portion 40 of the laminate sample 21 into and through the internal passage 34, or the laminate material sample 21 may be inserted by passing the proximal terminal portion 40 of the laminate sample 21 into and through the internal passage 34, leaving the distal terminal portion 40 projecting beyond the clamping fixture 20.

In order to facilitate the introduction of the desired pre-crack in the laminate material 21, the laminate material 21 may be positioned in the clamping fixture body 20 so that a distal edge 42 of the movable clamping portion 28 is aligned with a predetermined length of the planned pre-crack, at which point the movable clamping portion 28 may be translated toward the laminate material 21 in order to securely clamp the laminate material 21 between surface 29 and surface 33 of the movable clamping portion 28. In this way any crack or separation produced and/or extended by a separation of a first layer 44 and a second layer 46 of the laminate material 21 may be halted at the clamping fixture body 20, as the clamping force exerted on the laminate material 21 by the clamping fixture body 20 may prevent any further separation to occur between layers 44 and 46.

The clamping fixture body 20 may be positioned on the laminate material 21 at any position along the elongate laminate material 21 in order to terminate a forming pre-crack at that position. In one aspect of the disclosed method the laminate material 21 includes an initial interlaminar separation 50, and in such an aspect the clamping fixture body 20 may be positioned so that the distal edge 42 of movable clamping portion 28 is approximately 0.05 inches (1.3 mm) from the furthest extent of the initial interlaminar separation. For example, where the initial interlaminar separation is created by the presence of a thin film 52 between layers 44 and 46, the laminate material 21 may be positioned within the clamping fixture body 20 so that the distal edge 42 is disposed about 0.05 inches (1.3 mm) from the edge of the thin film.

The distal edge 42 of movable clamping portion 28 may be substantially straight, and may be oriented so that the edge is normal to (at right angles to) the lengthwise direction of the laminate material 21. Alternatively, or more preferably in addition, the distal edge 48 of base portion 22 may be substantially straight, and may be oriented so that the edge is normal to the lengthwise direction of the laminate material 21. In one embodiment of the disclosure, both of the distal edge 42 of movable clamping portion 28 and the distal edge 48 of base portion 22 are aligned with the predetermined length of the planned pre-crack, and therefore are necessarily in alignment with each other.

Although the clamping fixtures of the present disclosure may be manufactured from any material that provides sufficient strength, stiffness, and durability, the clamping fixtures are typically manufactured from a durable and high-strength metal or metal alloy, such as a stainless steel alloy. The components of the clamping fixture may be machined from the appropriate metal stock using any appropriate machining method, although the use of one or more CNC milling machines may be advantageous. Although the illustrative clamping fixture 20 is depicted as having a base portion 22 and a cap portion 24, the disclosed clamping fixtures may be composed of greater or fewer individual components, including for example a unitary clamping fixture body formed by machining an appropriate aperture through a single piece of metal stock.

The screws, bolts, and other fasteners of the illustrative clamping fixture 22 are intended to be illustrative only, and the clamping fixtures of the present disclosure may include different types, or a different number of such fasteners, without departing from the scope of the disclosure.

Example 2

Figure 6:
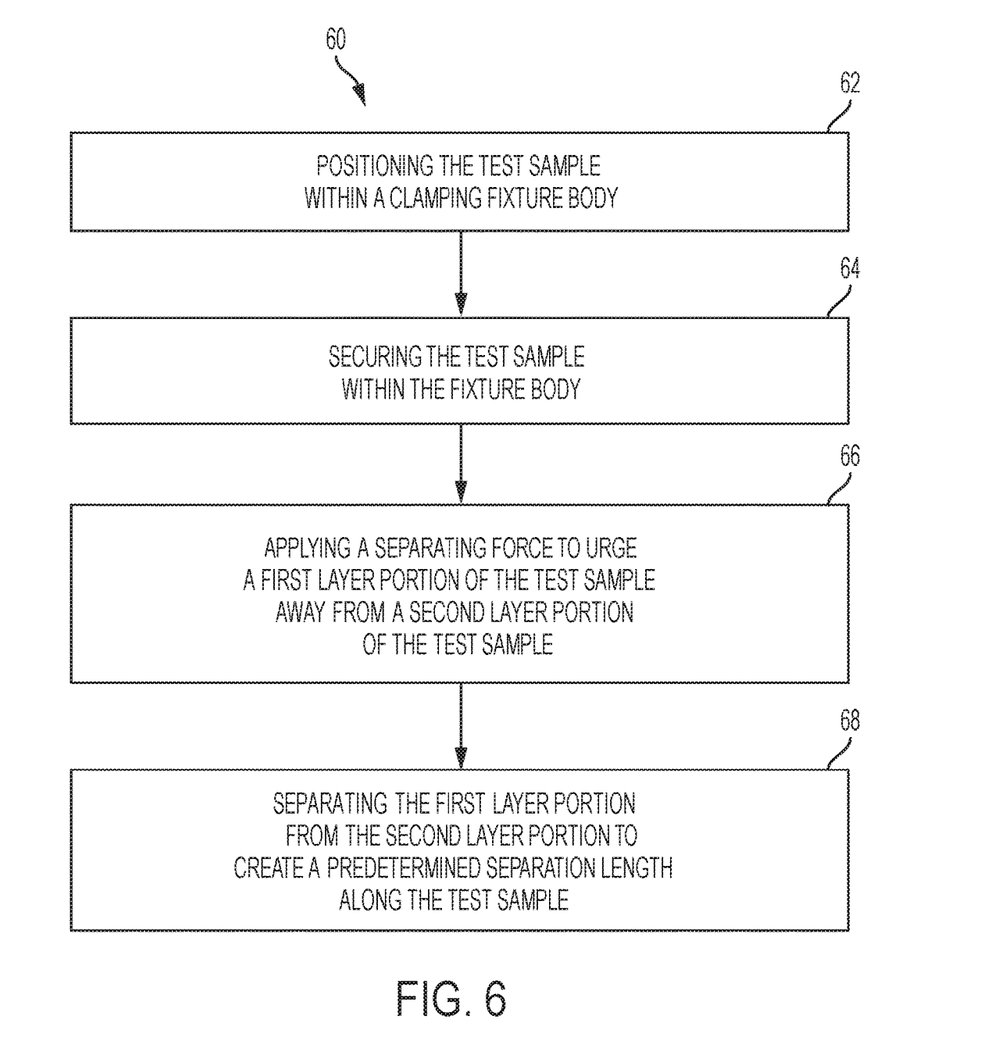
FIG. 6 is a flow chart depicting steps of a method for preparing a laminate material test sample, in accordance with aspects of the present disclosure.

This example describes an illustrative method of preparing a laminate material test sample, as shown in flowchart 60 of FIG. 6.

The method may include positioning the test sample within a clamping fixture body, as shown at 62; securing the test sample within the fixture body, as shown at 64; applying a separating force to urge a first layer portion of the test sample away from a second layer portion of the test sample, as shown at 66; and separating the first layer portion from the second layer portion to create a predetermined, or desired, separation length along the test sample, at 68. For the purposes of the present method, the predetermined separation length may be established by an interaction between the fixture body and the test sample as the first layer portion is separating from the second layer portion.

Example 3

Figure 7:
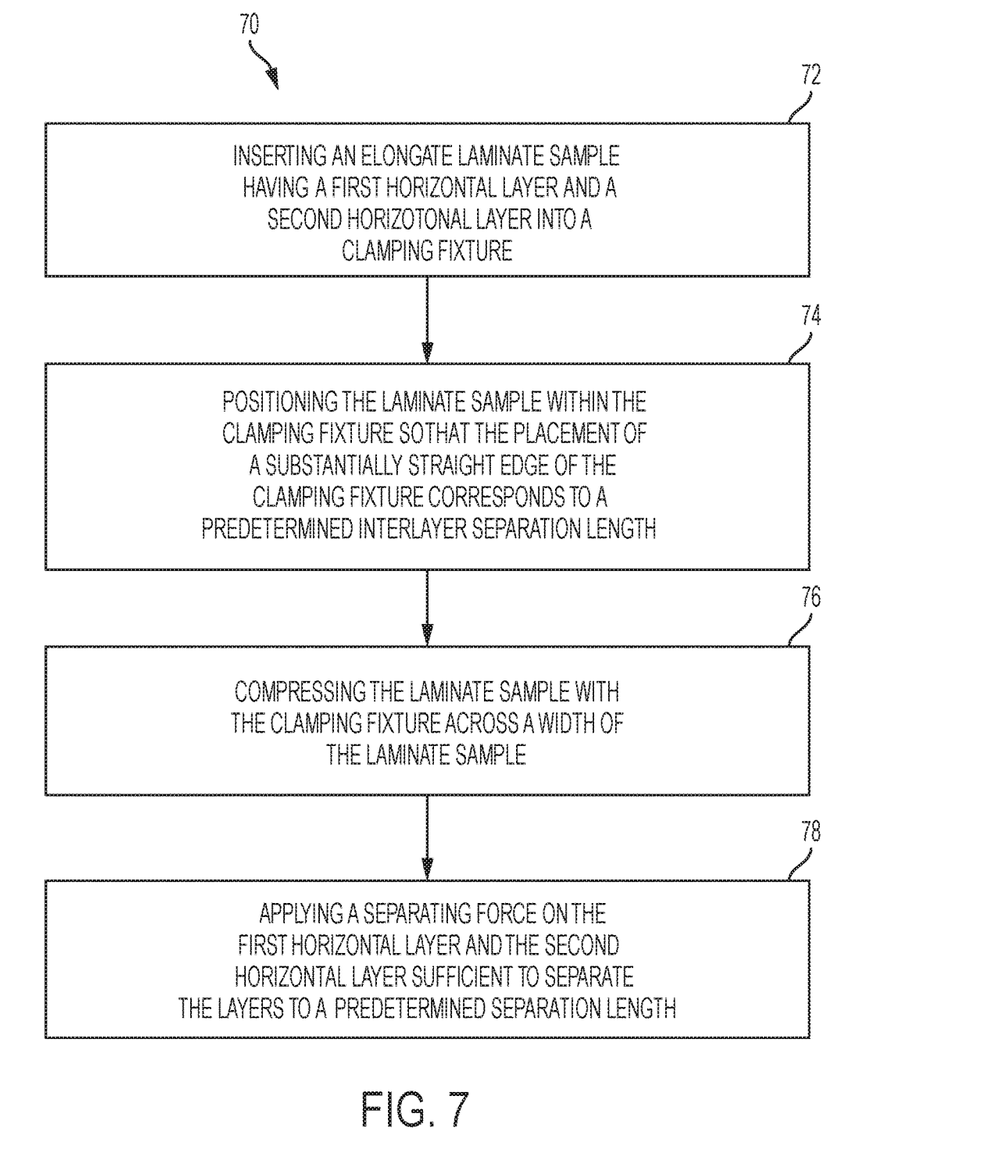
FIG. 7 is a flow chart depicting steps of a method for preparing an elongate laminate sample for interlayer adherence testing, in accordance with aspects of the present disclosure.

This example describes an illustrative method of preparing an elongate laminate sample for interlayer adherence testing, where the elongate laminate sample has at least a first horizontal layer and a second horizontal layer that are at least partially attached to one another, as shown in flowchart 70 of FIG. 7.

The method may include inserting the elongate laminate sample into a clamping fixture, where the clamping fixture is configured to substantially enclose the laminate sample on four sides orthogonal to the longitudinal axis, as shown at 72; positioning the laminate sample within the clamping fixture so that the placement of a substantially straight edge of the clamping fixture corresponds to a predetermined interlayer separation length, where the substantially straight edge of the clamping fixture is oriented normal to the longitudinal axis of the laminate sample, as shown at 74; compressing the laminate sample with the clamping fixture across a width of the laminate sample, as shown at 76; and applying a separating force on the first horizontal layer and the second horizontal layer sufficient to separate the layers to a predetermined separation length, as shown at 78.

Example 4

Figure 8:
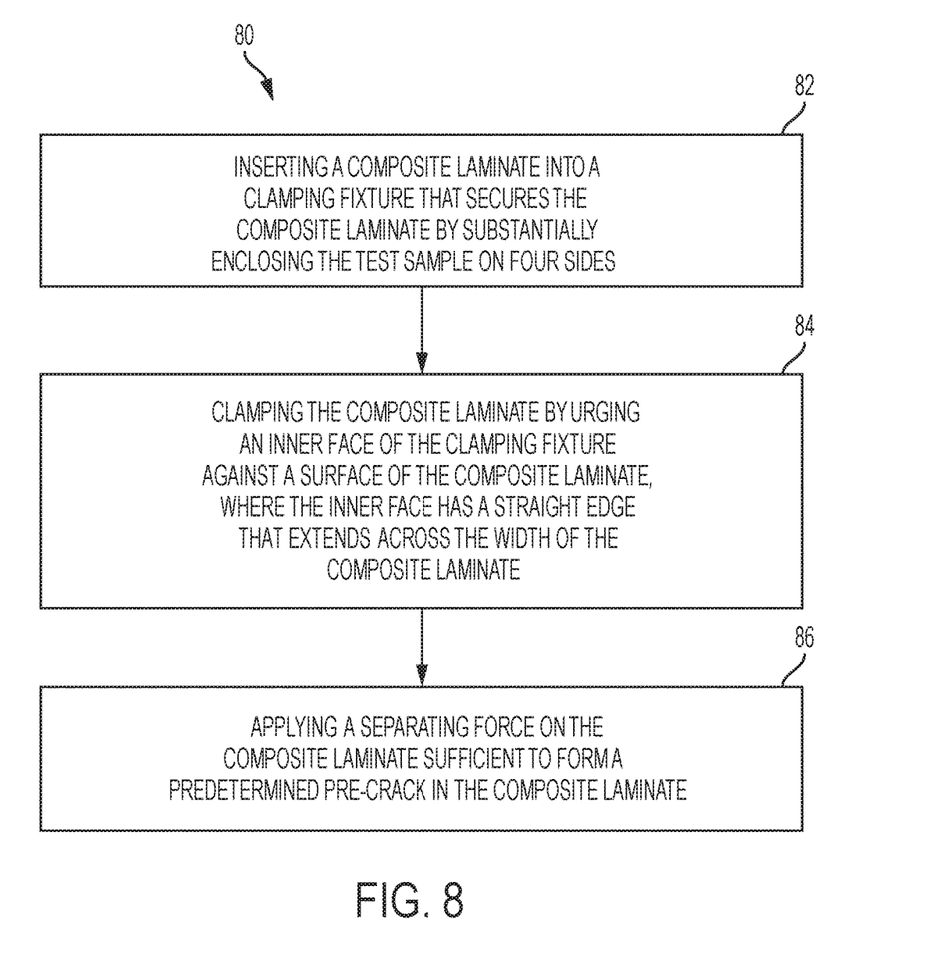
FIG. 8 is a flow chart depicting steps of a method for precracking a composite laminate, in accordance with aspects of the present disclosure.

This example describes an illustrative method of pre-cracking a composite laminate for a double cantilever beam adherence test, as shown in flowchart 80 of FIG. 8.

The method may include inserting the composite laminate into a clamping fixture, wherein the clamping fixture secures the test sample by substantially enclosing the composite laminate on four sides, as shown at 82; clamping the composite laminate by urging an inner face of the clamping fixture against a surface of the composite laminate, where the inner face has a straight edge that extends across the width of the composite laminate, as shown at 84; and applying a separating force on the composite laminate sufficient to form a predetermined precrack in the composite laminate, as shown at 86.

Example 5

This section describes additional aspects and features of methods of preparing laminate materials for testing according to the present disclosure, presented without limitation as a series of paragraphs, some or all of which may be alphanumerically designated for clarity and efficiency. Each of these paragraphs can be combined with one or more other paragraphs, and/or with disclosure from elsewhere in this application, in any suitable manner. Some of the paragraphs below expressly refer to and further limit other paragraphs, providing without limitation examples of some of the suitable combinations.

A1. A Method of Preparing a Laminate Material Test Sample, Comprising:

positioning the test sample within a fixture body;

securing the test sample within the fixture body;

applying a separating force to urge a first layer portion of the test sample away from a second layer portion of the test sample;

separating the first layer portion from the second layer portion to create a predetermined separation length along the test sample;

wherein the predetermined separation length is established by an interaction between the fixture body and the test sample as the first layer portion is separating from the second layer portion.

A2. The method of paragraph A1, wherein the laminate material test sample is defined by four surfaces including a length and a width, where the length is greater than the width.

A3. The method of paragraph A2, wherein the fixture body secures the test sample by substantially enclosing the test sample on each of four sides of the test sample, and an outer edge of the fixture body is normal to the lengthwise direction of the test sample.

A4. The method of paragraph A1, wherein the initial separation is substantially straight and substantially normal to the lengthwise direction of the test sample.

A5. The method of paragraph A1, further comprising using the fixture body to prepare one or more additional laminate material test samples to have essentially equal separation lengths.

B1. A method of preparing an elongate laminate sample for interlayer adherence testing, the laminate sample having at least a first horizontal layer and a second horizontal layer that are at least partially attached to one another, the method comprising:

inserting the elongate laminate sample into a clamping fixture, wherein the clamping fixture is configured to substantially enclose the laminate sample on four sides orthogonal to the longitudinal axis;

positioning the laminate sample within the clamping fixture so that a placement of a substantially straight edge of the clamping fixture corresponds to a predetermined interlayer separation length, wherein the substantially straight edge of the clamping fixture is oriented at normal to the longitudinal axis of the laminate sample;

compressing the laminate sample with the clamping fixture across a width of the laminate sample;

applying a separating force on the first horizontal layer and the second horizontal layer sufficient to separate the layers to a predetermined separation length.

B2. The method of paragraph B1, wherein the first horizontal layer and the second horizontal layer are attached to one another by an adhesive.

B3. The method of paragraph B1, wherein at least one of the first horizontal layer and the second horizontal layer include a composite material.

B4. The method of paragraph B1, wherein along at least a terminal portion of the laminate sample the first horizontal layer and the second horizontal layer are not attached to one another.

B5. The method of paragraph B4, wherein for at least part of the terminal portion of the laminate sample the first horizontal layer and the second horizontal layer are separated by a thin film.

B6. The method of paragraph B5, wherein the film includes a polyfluorinated polymer.

B7. The method of paragraph B1, wherein the clamping fixture defines a passage configured to accept the laminate sample, and inserting the laminate sample into the clamping fixture includes extending a terminal portion of the laminate sample through the passage to project beyond the clamping fixture.

B8. The method of paragraph B7, wherein the clamping fixture includes an adjustably movable block having a width substantially equivalent to both the width of the passage and the width of the laminate sample, and compressing the laminate sample includes urging the movable block against the laminate sample.

B9. The method of paragraph B8, wherein the adjustably movable block may be urged against the laminate sample by rotating a threaded actuator.

C1. A method of precracking a composite laminate for a double cantilever beam adherence test, comprising:

inserting the composite laminate into a clamping fixture, wherein the clamping fixture secures the test sample by substantially enclosing the test sample on four sides;

clamping the composite laminate by urging a first inner face of the clamping fixture against a surface of the composite laminate, wherein the first inner face has a straight edge that extends across a width of the composite laminate; and applying a separating force on the composite laminate sufficient to form a predetermined precrack in the composite laminate.

C2. The method of paragraph C1, further comprising positioning the clamping fixture so that the straight edge of the first inner face corresponds to a predetermined precrack length.

C3. The method of paragraph C2, wherein the composite laminate initially incorporates a partial layer separation, and applying the separating force on the composite laminate extends the partial layer separation to the predetermined precrack length.

C4. The method of paragraph C2, wherein the method provides a substantially reproducible precrack in a plurality of composite laminates.

C5. The method of paragraph C1, wherein the clamping fixture defines a passage configured to accept the composite laminate, and inserting the composite laminate into the clamping fixture includes extending a terminal portion of the composite laminate through the passage to project beyond the clamping fixture.

C6. The method of paragraph C1, wherein a straight edge of the first inner face of the clamping fixture aligns with a straight edge of a second opposing inner face of the clamping fixture, such that clamping the composite laminate includes clamping the composite laminate between the first inner face and the second opposing inner face such that the straight edges of the two faces align with a predetermined precrack length.

C7. The method of paragraph C6, wherein the first inner face of the clamping fixture comprises an adjustably movable block having a width substantially equivalent to the width of the composite laminate, and compressing the composite laminate includes urging the movable block to compress the composite laminate against the second inner face.

Advantages, Features, Benefits

The various embodiments of methods of preparing laminate material test samples described herein may provide several advantages over previous methods for preparing laminate materials for interlaminar fracture testing.

In particular, by using the disclosed clamping fixture, a pre-crack having a predetermined crack length can be formed in an adhesive-bonded laminate composite. The clamping fixture can be quickly and accurately positioned on the laminate composite, and may form a consistent and highly repeatable initiation crack in the composite material, thereby removing any effects due to variance in the initial force required to initiate such a crack. In this way the presently disclosed methods may be used to create substantially reproducible pre-cracks in a plurality of composite laminates.

The disclosed method replaces previous methods of forming a pre-crack which resulted in variability in pre-crack formation, as well as requiring significantly more time. As a result, the accuracy of placement of the pre-crack is enhanced, and tedious and time-consuming manual manipulations are eliminated, and the clamping fixture's size and geometry provides balanced in-line loading to the test sample.

CONCLUSION

While various methods of preparing laminate material test samples have been particularly shown and described with reference to preferred embodiments thereof, it will be understood by those skilled in the art that various other changes in the form and details may be made therein without departing from the spirit and scope of the disclosure. The foregoing description of the exemplary embodiments of the disclosure has been presented for purposes of illustration and description. It is not intended to be exhaustive or to limit the disclosure to the precise form disclosed. Man modifications and variations are possible in light of the above teaching. It is intended that the scope of the disclosure be limited not with this detailed description but rather by the claims appended hereto.

The subject matter of the disclosure(s) includes all novel and nonobvious combinations and subcombinations of the various elements, features, functions, and/or properties disclosed herein. The following claims particularly point out certain combinations and subcombinations regarded as novel and nonobvious. Embodiment(s) embodied in other combinations and subcombinations of features, functions, elements, and/or properties may be claimed in applications claiming priority from this or a related application. Such claims, whether directed to a different embodiment or to the same embodiment, and whether broader, narrower, equal, or different in scope to the original claims, also are regarded as included within the subject matter of the present disclosure.

We claim:

1. A method of preparing a laminate material test sample having a laminar interface, comprising:
    determining a desired interlaminar separation length;
    positioning the test sample within a fixture body so that a distance of a distal edge of the fixture body from a terminal end of the laminate material test sample is equal to the desired interlaminar separation length;
    securing the test sample within the fixture body by compressing the test sample using the fixture body along an axis perpendicular to the laminar interface and across its width;
    applying a separating force to urge a first layer portion of the test sample away from a second layer portion of the test sample in an initial separation;
    separating the first layer portion from the second layer portion up to the distal edge in order to create the determined separation length.

2. The method of claim 1, wherein the laminate material test sample is defined by four surfaces including a length and a width, where the length is greater than the width.

3. The method of claim 2, wherein the fixture body secures the test sample by substantially enclosing the test sample on each of four sides of the test sample, and an outer edge of the fixture body is normal to a lengthwise direction of the test sample.

4. The method of claim 1, wherein the initial separation is substantially straight and substantially normal to a lengthwise direction of the test sample.

5. The method of claim 1, further comprising using the fixture body to repeat the steps of positioning the test sample, securing the test sample, applying the separating force, and separating the first and second layer portions on one or more additional laminate material test samples to create equal separation lengths in the additional laminate material test samples.

6. A method of preparing an elongate laminate sample for interlayer adherence testing, the laminate sample having at least a first horizontal layer and a second horizontal layer that are at least partially attached to one another at a laminar interface, the method comprising:
  selecting a desired interlayer separation length;
  inserting the elongate laminate sample into a clamping fixture, wherein the clamping fixture is configured to substantially enclose the laminate sample on four sides orthogonal to a longitudinal axis of the laminate sample;
  positioning the laminate sample within the clamping fixture so that a distance of a substantially straight distal edge of the clamping fixture from a terminal end of the laminate sample is equal to the selected desired interlayer separation length, wherein the substantially straight edge of the clamping fixture is oriented normal to the longitudinal axis of the laminate sample;
  compressing the laminate sample with the clamping fixture along an axis perpendicular to the laminar interface and across a width of the laminate sample;
  applying a separating force on the first horizontal layer and the second horizontal layer sufficient to separate the layers to the selected interlayer separation length.

7. The method of claim 6, wherein the first horizontal layer and the second horizontal layer are attached to one another by an adhesive.

8. The method of claim 6, wherein at least one of the first horizontal layer and the second horizontal layer includes a composite material.

9. The method of claim 6, wherein along at least a terminal portion of the laminate sample the first horizontal layer and the second horizontal layer are not attached to one another.

10. The method of claim 9, wherein for at least part of the terminal portion of the laminate sample the first horizontal layer and the second horizontal layer are separated by a thin film.

11. The method of claim 10, wherein the film includes a polyfluorinated polymer.

12. The method of claim 6, wherein the clamping fixture defines a passage configured to accept the laminate sample, and inserting the laminate sample into the clamping fixture includes extending a terminal portion of the laminate sample through the passage to project beyond the clamping fixture.

13. The method of claim 12, wherein the clamping fixture includes an adjustably movable block having a width substantially equivalent to both the width of the passage and the width of the laminate sample, and compressing the laminate sample includes urging the movable block against the laminate sample.

14. The method of claim 13, wherein the adjustably movable block can be urged against the laminate sample by rotating a threaded actuator.

15. A method of precracking a composite laminate having a laminar interface for a double cantilever beam adherence test, comprising:
  inserting the composite laminate into a clamping fixture, wherein the clamping fixture secures the test sample by substantially enclosing the test sample on four sides;
  clamping the composite laminate along an axis perpendicular to the laminar interface by urging a first inner face of the clamping fixture against a surface of the composite laminate, wherein the first inner face has a straight edge that extends across a width of the composite laminate; and
  applying a separating force on the composite laminate sufficient to form a predetermined precrack in the composite laminate.

16. The method of claim 15, further comprising positioning the clamping fixture so that the straight edge of the first inner face is disposed at a distance from a terminal end of the composite laminate that substantially equals a predetermined precrack length.

17. The method of claim 16, wherein the composite laminate initially incorporates a partial layer separation, and applying the separating force on the composite laminate extends the partial layer separation to the predetermined precrack length.

18. The method of claim 16, wherein the method provides a substantially reproducible precrack in a plurality of composite laminates.

19. The method of claim 15, wherein the clamping fixture defines a passage configured to accept the composite laminate, and inserting the composite laminate into the clamping fixture includes extending a terminal portion of the composite laminate through the passage to project beyond the clamping fixture.

20. The method of claim 15, further comprising aligning the straight edge of the first inner face of the clamping fixture with a straight edge of a second opposing face of the clamping fixture, such that clamping the composite laminate includes clamping the composite laminate between the first inner face and the second opposing face such that the straight edges of the two faces align with a predetermined precrack length.

21. The method of claim 20, wherein the first inner face of the clamping fixture comprises an adjustably movable block having a width substantially equivalent to the width of the composite laminate, and clamping the composite laminate includes urging the movable block to compress the composite laminate against the second inner face.

\* \* \* \* \*